US009510593B2

United States Patent
Nagasawa et al.

(10) Patent No.: US 9,510,593 B2
(45) Date of Patent: Dec. 6, 2016

(54) S-BENZYLTHIOURACIL COMPOUNDS AND METHODS OF ENHANCING PLANT ROOT GROWTH

(71) Applicant: Valent BioSciences Corporation, Libertyville, IL (US)

(72) Inventors: Asako Nagasawa, Hyogo (JP); Franklin Paul Silverman, Highland Park, IL (US); Daniel F. Heiman, Libertyville, IL (US); Dale O. Wilson, Jr., Round Lake Beach, IL (US); Peter D. Petracek, Grayslake, IL (US); Fujio Mukumoto, Hyogo (JP); Hiroaki Tamaki, Hyogo (JP); Takashi Moriwaki, Hyogo (JP)

(73) Assignee: Valent BioSciences Corporation, Libertyville, IL (US)

( * ) Notice: Subject to any disclaimer, the term of this patent is extended or adjusted under 35 U.S.C. 154(b) by 2 days.

(21) Appl. No.: 14/596,687

(22) Filed: Jan. 14, 2015

(65) Prior Publication Data

US 2015/0201620 A1    Jul. 23, 2015

Related U.S. Application Data

(60) Provisional application No. 61/928,712, filed on Jan. 17, 2014.

(51) Int. Cl.
| | |
|---|---|
| *A01N 43/54* | (2006.01) |
| *A01N 43/90* | (2006.01) |
| *C07D 239/47* | (2006.01) |
| *C07D 239/52* | (2006.01) |
| *C07D 239/56* | (2006.01) |
| *C07D 473/22* | (2006.01) |
| *C07D 239/60* | (2006.01) |

(52) U.S. Cl.
CPC ............ *A01N 43/54* (2013.01); *A01N 43/90* (2013.01); *C07D 239/47* (2013.01); *C07D 239/52* (2013.01); *C07D 239/56* (2013.01); *C07D 239/60* (2013.01); *C07D 473/22* (2013.01)

(58) Field of Classification Search
CPC ........ A01N 43/54; A01N 25/10; A01N 43/40; A01N 43/56; A01N 43/60; A01N 25/08; A01N 51/00
See application file for complete search history.

(56) References Cited

U.S. PATENT DOCUMENTS

| 5,599,770 A | 2/1997 | Kubota et al. |
| 5,723,412 A | 3/1998 | Kanno et al. |
| 2013/0267564 A1 | 10/2013 | Kasahara et al. |

FOREIGN PATENT DOCUMENTS

| JP | 0559015 | * | 3/1993 | ............ A01N 43/54 |
| JP | H05-59015 | | 3/1993 | |
| JP | H 0559015 | | 3/1993 | |

OTHER PUBLICATIONS

JP0559015, published 1993, Yoshinori et al.*
ISR and Written Opinion in corresponding Application No. PCT/US2015/011352 issued Apr. 3, 2015.
Sato et al., "Characterization of four molybdenum cofactor mutants of rice, *Oryza sativa* L." Plant Science 1996, 119, pp. 39-47.
Hoagland et al., "The water-culture method for growing plants without soil", California Agricultural Experiment Station, Jan. 1950, Circular 347, pp. 1-32.

* cited by examiner

*Primary Examiner* — Audrea Buckley
(74) *Attorney, Agent, or Firm* — Wood, Phillips, Katz, Clark & Mortimer

(57) ABSTRACT

The present invention is directed to methods for enhancing root growth comprising applying a S-Benzylthiouracil compound, or a salt thereof, to a plant, plant propagation material, root zone, or root of a plant. The invention also relates to methods for reducing the harmful effects of environmentally stressful conditions on plants, such as drought, or intense temperatures, by application of a S-Benzylthiouracil compound, or a salt thereof, to a plant, plant propagation material, root zone, or root of a plant. The invention further relates to new S-Benzylthiouracil derivatives, and salts thereof.

13 Claims, No Drawings

S-BENZYLTHIOURACIL COMPOUNDS AND METHODS OF ENHANCING PLANT ROOT GROWTH

CROSS-REFERENCE TO RELATED APPLICATION

This application claims priority of U.S. Provisional Application 61/928,712 filed Jan. 17, 2014, the disclosure of which is incorporated herein by reference.

FIELD OF THE INVENTION

The invention relates to S-Benzylthiouracil compounds and methods of using S-Benzylthiouracil compounds to enhance the growth of plant roots.

BACKGROUND OF THE INVENTION

Plant roots are critical organs of vascular plant species. It is well known that roots provide water uptake while physical support to the plant. Roots also extract mineral and organic nutrients from the soil or growth medium, and produce a number of important natural products, such as hormones and defense compounds that impact plant growth and development. Roots may act as a storage organ for nutrients or contain chemicals that are pharmaceutically important. Establishment of an appropriate root structure is important for the plant to maximize its growth potential and production.

Due to the complexity of the development of plant roots, it has been difficult to identify mechanisms to enhance root growth while maintaining the health of the entire plant. The processes that lead to increased root growth involve multiple mechanisms of cellular adaptation and numerous metabolic pathways. In addition, a pathway that increases root growth may negatively impact shoot, stem or leaf growth.

During their life cycle, plants may be at risk for exposure to environmentally stressful conditions. These conditions can include limited access to water (such as drought), or exposure to high or low temperatures. If the duration or severity of these stressful conditions is too great, the exposed plants may have reduced growth and yield. While plants have mechanisms to mitigate the effects of environmentally stressful conditions, continuous exposure may cause damage to the plants and can result in death of the plant. Reduced crop yield or death of crop plants due to environmentally stressful conditions is a major concern of crop plant growers.

Strong root growth allows for the plants to be more competitive with surrounding plants, such as weeds, for water and nutrient resources. This is especially true in areas where the plant might be exposed to environmentally stressful conditions. An enhanced root structure would allow the plants to increase their access to water and nutrients. Longer roots would allow the roots to reach new areas of the soil or growth medium. A larger root system provides a greater surface area for absorption of water and nutrients.

Therefore, there is a need in the art for compounds and methods to enhance root growth. There is a need for enhanced root growth that provides healthier and higher yielding plants. There is a need for enhanced root growth that provides protection to the plants from environmentally stressful conditions, such as drought or intense temperatures.

SUMMARY OF THE INVENTION

In one aspect, the invention is directed to methods for enhancing monocotyledonous and dicotyledonous plant growth comprising applying to a plant, plant propagation material, root zone, or root of a monocotyledonous or dicotyledonous plant one or more compounds selected from the group consisting of S-Benzylthiouracil and S-Benzylthiouracil compounds of Formula I:

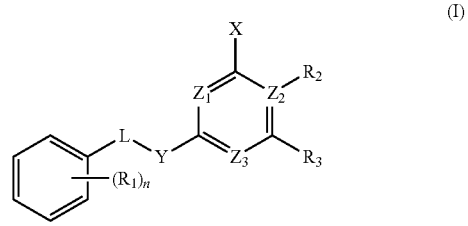

wherein X is OH, $NH_2$, or H; Y is S or O; $Z_1$, $Z_2$, and $Z_3$ are each carbon or N, but at least two of $Z_1$, $Z_2$, and $Z_3$ are N; L is —$CH_2$—, —$CH_2CH_2$—, or —CH=$CHCH_2$—; $R_3$ is H, lower alkyl, or OH; and n is 0, 1, or 2, wherein when n is 0, $R_1$ is absent, when n is 1, $R_1$ is H, halogen, lower alkyl, or lower alkoxy in the 2-, 3- or 4-position and wherein when n is 2, each $R_1$ is independently selected from halogen, lower alkyl or lower alkoxy; $R_2$ is H, lower alkyl, —COO-lower alkyl, taken together with $R_3$ constitutes a —N=CH—NH— bridge forming a ring, or is absent when $Z_2$ is N; wherein $Z_2$ is carbon when $R_2$ is H, lower alkyl or —COO-lower alkyl and when $R_2$ and $R_3$ taken together constitute a —N=CH—NH— bridge to form a ring; or a salt thereof.

In a further aspect, the invention is directed to methods for enhancing monocotyledonous or dicotyledonous plant growth comprising applying to a plant, plant propagation material, root zone, or root of a monocotyledonous or dicotyledonous plant the S-Benzylthiouracil compounds of Formula I, wherein n is 1, $R_1$ is 3-F, L is —$CH_2$—, Y is S, $R_2$ is H, $R_3$ is H, $Z_1$ is N, $Z_2$ is carbon, $Z_3$ is N, and X is OH (Compound 1); or a potassium salt thereof.

In a further aspect of the invention, the methods are directed to reducing the harmful effects of drought or high or low temperatures comprising applying to a plant, plant propagation material, root zone, or root of a monocotyledonous or dicotyledonous plant the S-Benzylthiouracil compounds of Formula I, wherein n is 1, $R_1$ is 3-F, L is —$CH_2$—, Y is S, $R_2$ is H, $R_3$ is H, $Z_1$ is N, $Z_2$ is carbon, $Z_3$ is N, and X is OH (Compound 1); or a salt thereof.

In an additional aspect, the invention is directed to S-Benzylthiouracil derivatives selected from the group consisting of S-Benzylthiouracil compounds of Formula I where n is 2, $R_1$ is 3,4-diF, L is —$CH_2$—, Y is S, $R_2$ is H, $R_3$ is H, $Z_1$ is N, $Z_2$ is carbon, $Z_3$ is N, and X is OH (Compound 5);

n is 2, $R_1$ is 3,5-diF, L is —$CH_2$—, Y is S, $R_2$ is H, $R_3$ is H, $Z_1$ is N, $Z_2$ is carbon, $Z_3$ is N, and X is OH (Compound 6);

n is 1, $R_1$ is 3-F, $R_2$ is —COO-ethyl, L is —$CH_2$—, Y is S, $Z_1$ is N, $Z_2$ is carbon, $Z_3$ is N, and X is OH (Compound 12);

n is 1, $R_1$ is 2-methyl, $R_2$ is H, $R_3$ is methyl, L is —$CH_2$—, Y is S, $Z_1$ is N, $Z_2$ is carbon, $Z_3$ is N, and X is OH (Compound 14);

n is 2, $R_1$ is 2,6-diCl, $R_2$ is H, $R_3$ is methyl, L is —$CH_2$—, Y is S, $Z_1$ is N, $Z_2$ is carbon, $Z_3$ is N, and X is OH (Compound 16);

n is 1, $R_1$ is 3-F, $R_2$ is H, $R_3$ is H, L is —$CH_2$—, Y is S, $Z_1$ is N, $Z_2$ is carbon, $Z_3$ is N, and X is $NH_2$ (Compound 19);

n is 1, $R_1$ is 3-F, Y is O, L is —$CH_2$—, $R_2$ is H, $R_3$ is H, $Z_1$ is N, $Z_2$ is carbon, $Z_3$ is N, and X is OH (Compound 21); and n is 0 ($R_1$ is absent), Y is O, L is —$CH_2$—, $R_2$ is H, $R_3$ is H, $Z_1$ is N, $Z_2$ is carbon, $Z_3$ is N, and X is OH (Compound 24), or a salt thereof.

DETAILED DESCRIPTION OF THE INVENTION

The present invention is directed to methods for enhancing root growth comprising applying at least one S-Benzylthiouracil compound to a plant propagation material, to the root zone or roots of plants, or to plants. As used herein, "S-Benzylthiouracil compound" or "S-Benzylthiouracil compounds" includes unsubstituted S-Benzylthiouracil, or an analog or a derivative thereof, unless specifically indicated otherwise.

As used herein, "S-Benzylthiouracil" refers only to the unsubstituted compound (2-[(phenylmethyl)thio]-4(3H)-pyrimidinone [31167-21-2]), which has the following structure:

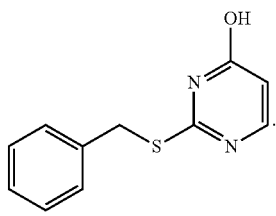 [SMILES: Oc1ccnc(SCc2ccccc2)n1 ; "."]

Applicants unexpectedly found that S-Benzylthiouracil enhanced root growth. Applicants then unexpectedly found that some S-Benzylthiouracil derivatives, analogs, and salts thereof, also provided root enhancement. However, Applicants were surprised to find that not all S-Benzylthiouracil derivatives, analogs, and salts thereof, provided root enhancement. The effect of the derivatives and analogs was unpredictable and could not be determined without experimentation. For example, when applied to mungbean in a pouch assay, Applicants found that for a S-Benzylthiouracil compound with a methyl group on the 6-position of the uracil ring, the root enhancement effect was unexpectedly very high at over 36 percent enhancement (see Table 10 below). Applicants also found that halogen substituted benzyl ring S-Benzylthiouracil compounds provided over 10 percent enhancement of root growth (see Table 9 below). Applicants expected that a compound with both of these substitutions would result in an increased root growth that was more than either substitution's effect alone. In contrast, they found that if a S-Benzylthiouracil compound has a methyl group on the 6-position of the uracil moiety and a halogen benzyl ring substitution, the root enhancement effect was only around 8 percent (see Table 10) on mungbean. Accordingly, Applicants found that merely looking at the structure of the S-Benzylthiouracil compounds was not an accurate way to determine the effects that the compound would have on root growth.

Applicants also found that the S-Benzylthiouracil compounds' effects were specific to monocotyledonous versus dicotyledonous plants. For example, S-Benzylthiouracil with a 3-F substitution on the benzyl ring (Compound 1) provided the greatest root enhancement on rice (19.8 percent, see Table 1 below). However, Compound 1 only provided a root enhancement effect of 10.4 percent that was about half the effect of unsubstituted S-Benzylthiouracil ("Compound 2") (increase of 18.9 percent) when applied to mungbean (see Table 11 below). After determining the effect of one S-Benzylthiouracil compound on a plant species, Applicants were not able to predict the effect that compound, or structurally similar compounds, would have on the other flowering plant class (i.e., monocot or dicot) without experimentation. Accordingly, Applicants' methods were unexpected.

In the prior art literature discussing 2-thiouracil and compounds related to it, several different structural representations are commonly encountered. These represent the possible tautomeric forms of the compounds, which are in equilibrium with each other as indicated in the scheme below:

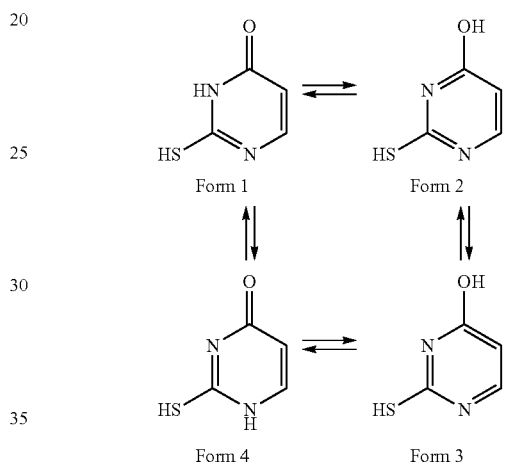

For consistency and simplicity we represent the compounds of the present invention using Form 2 or Form 3 throughout the application, but that is in no way meant to exclude the structures represented by the other tautomeric forms.

In one embodiment, the invention is directed to methods for enhancing monocotyledonous plant root growth comprising applying to a plant, plant propagation material, root zone, or root of a monocotyledonous plant one or more compounds selected from the group consisting of S-Benzylthiouracil compounds of Formula I:

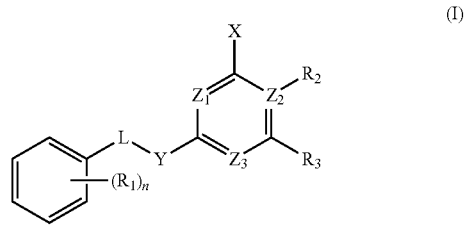

wherein X is OH, $NH_2$, or H; Y is S or O; $Z_1$, $Z_2$, and $Z_3$ are each carbon or N, but at least two of $Z_1$, $Z_2$, and $Z_3$ are N; L is —$CH_2$—, —$CH_2CH_2$—, or —$CH=CHCH_2$—; $R_3$ is H, lower alkyl, or OH; and n is 0, 1, or 2, wherein when n is 0, $R_1$ is absent, when n is 1, $R_1$ is H, halogen, lower alkyl, or lower alkoxy in the 2-, 3- or 4-position, and wherein when n is 2, each $R_1$ is independently selected from halogen, lower alkyl or lower alkoxy; $R_2$ is H, lower alkyl, —COO-lower alkyl, taken together with $R_3$ constitutes a —N=CH—NH— bridge forming a ring, or is absent when $Z_2$ is N; wherein $Z_2$ is carbon when $R_2$ is H, lower alkyl or —COO-lower alkyl and when $R_2$ and $R_3$ taken together constitute a —N=CH—NH— bridge to form a ring; or a salt thereof.

In a preferred embodiment, the plants are monocotyledonous and the compounds are of Formula I, wherein n is 1 or 2, when n is 1, $R_1$ is halogen, or lower alkoxy, and when n is 2, each $R_1$ is halogen, L is —$CH_2$—, Y is S, $R_2$ is H, $R_3$ is H, $Z_1$ is N, $Z_2$ is carbon, $Z_3$ is N, and X is OH, or a salt thereof. In a more preferred embodiment, when n is 2, $R_1$ is in the 2,3-, 2,4-, 2,5-, 2,6-, 3,4- or 3,5-positions.

In a more preferred embodiment of the invention, the plants are monocotyledonous and the compounds are of Formula I where n is 1, $R_1$ is 3-F, L is —$CH_2$—, Y is S, $R_2$ is H, $R_3$ is H, $Z_1$ is N, $Z_2$ is carbon, $Z_3$ is N, and X is OH (Compound 1);

n is 0 ($R_1$ is absent), L is —$CH_2$—, Y is S, $R_2$ is H, $R_3$ is H, $Z_1$ is N, $Z_2$ is carbon, $Z_3$ is N, and X is OH (Compound 2);

n is 1, $R_1$ is 4-F, L is —$CH_2$—, Y is S, $R_2$ is H, $R_3$ is H, $Z_1$ is N, $Z_2$ is carbon, $Z_3$ is N, and X is OH (Compound 3);

n is 1, $R_1$ is 2-F, L is —$CH_2$—, Y is S, $R_2$ is H, $R_3$ is H, $Z_1$ is N, $Z_2$ is carbon, $Z_3$ is N, and X is OH (Compound 4);

n is 2, $R_1$ is 3,4-diF, L is —$CH_2$—, Y is S, $R_2$ is H, $R_3$ is H, $Z_1$ is N, $Z_2$ is carbon, $Z_3$ is N, and X is OH (Compound 5);

n is 2, $R_1$ is 3,5-diF, L is —$CH_2$—, Y is S, $R_2$ is H, $R_3$ is H, $Z_1$ is N, $Z_2$ is carbon, $Z_3$ is N, and X is OH (Compound 6);

n is 1, $R_1$ is 3-MeO, L is —$CH_2$—, Y is S, $R_2$ is H, $R_3$ is H, $Z_1$ is N, $Z_2$ is carbon, $Z_3$ is N, and X is OH (Compound 7), or n is 1, $R_1$ is 4-MeO, L is —$CH_2$—, Y is S, $R_2$ is H, $R_3$ is H, $Z_1$ is N, $Z_2$ is carbon, $Z_3$ is N, and X is OH (Compound 8), or a salt thereof.

In an embodiment, the plants are monocotyledonous and the compounds are of Formula I where n is 1, $R_1$ is F, L is —$CH_2$—, Y is S, $R_2$ is H, $R_3$ is H, $Z_1$ is N, $Z_2$ is carbon, $Z_3$ is N, and X is OH, or a salt thereof. Preferably, $R_1$ is 3-F.

In another embodiment, the plants are monocotyledonous and the compounds are of Formula I where n is 0 and $R_1$ is absent, or n is 1 and $R_1$ is 3-F or 2-methyl, or n is 2 and $R_1$ is 2,6-diCl; L is —$CH_2$—; Y is S; and $Z_1$ is N, or a salt thereof.

In a preferred embodiment, the plants are monocotyledonous and the compounds are of Formula I where n is 0 ($R_1$ is absent), $R_2$ is H, $R_3$ is OH, L is —$CH_2$—, Y is S, $Z_1$ is N, $Z_2$ is carbon, $Z_3$ is N, and X is OH (Compound 10);

n is 1, $R_1$ is 3-F, $R_2$ is H, $R_3$ is H, L is —$CH_2$—, Y is S, $Z_1$ is N, $Z_2$ is N, $Z_3$ is carbon, and X is OH (Compound 11);

n is 1, $R_1$ is 3-F, $R_2$ is —COO-ethyl, L is —$CH_2$—, Y is S, $Z_1$ is N, $Z_2$ is carbon, $Z_3$ is N, and X is OH (Compound 12);

n is 1, $R_1$ is 3-F, $R_2$ and $R_3$ taken together constitute a —N=CH—NH— bridge forming a ring, L is —$CH_2$—, Y is S, $Z_1$ is N, $Z_2$ is carbon, $Z_3$ is N, and X is OH (Compound 13);

n is 1, $R_1$ is 2-methyl, $R_2$ is H, $R_3$ is methyl, L is —$CH_2$—, Y is S, $Z_1$ is N, $Z_2$ is carbon, $Z_3$ is N, and X is OH (Compound 14);

n is 0 ($R_1$ is absent), $R_2$ is H, $R_3$ is H, L is —$CH_2$—, Y is S, $Z_1$ is N, $Z_2$ is carbon, $Z_3$ is N, and X is OH (Compound 15);

n is 2, $R_1$ is 2,6-diCl, $R_2$ is H, $R_3$ is methyl, L is —$CH_2$—, Y is S, $Z_1$ is N, $Z_2$ is carbon, $Z_3$ is N, and X is OH (Compound 16);

n is 1, $R_1$ is 3-F, $R_2$ is H, $R_3$ is H, L is —$CH_2$—, Y is S, $Z_1$ is N, $Z_2$ is carbon, $Z_3$ is N, and X is H (Compound 17);

n is 1, $R_1$ is 3-F, $R_2$ is H, $R_3$ is OH, L is —$CH_2$—, Y is S, $Z_1$ is N, $Z_2$ is carbon, and $Z_3$ is N, and X is OH (Compound 18); or n is 1, $R_1$ is 3-F, $R_2$ is H, $R_3$ is H, L is —$CH_2$—, Y is S, $Z_1$ is N, $Z_2$ is carbon, $Z_3$ is N, and X is $NH_2$ (Compound 19), or a salt thereof.

In another embodiment, the plants are monocotyledonous and the invention is directed to methods of applying an S-Benzylthiouracil compound of Formula I wherein n is 0, or n is 1 and $R_1$ is 3-F, $R_2$ is H, $R_3$ is H, $Z_1$ is N, $Z_2$ is carbon, $Z_3$ is N, and X is OH, or a salt thereof.

In a preferred embodiment, the plants are monocotyledonous and the S-Benzylthiouracil compounds are of Formula I wherein n is 1, $R_1$ is 3-F, Y is O, L is —$CH_2$—, $R_2$ is H, $R_3$ is H, $Z_1$ is N, $Z_2$ is carbon, $Z_3$ is N, and X is OH (Compound 21);

n is 0 ($R_1$ is absent), Y is S, L is —$CH_2CH_2$—, $R_2$ is H, $R_3$ is H, $Z_1$ is N, $Z_2$ is carbon, $Z_3$ is N, and X is OH (Compound 22);

n is 0 ($R_1$ is absent), Y is S, L is —CH=CH$CH_2$—, $R_2$ is H, $R_3$ is H, $Z_1$ is N, $Z_2$ is carbon, $Z_3$ is N, and X is OH (Compound 23); or n is 0 ($R_1$ is absent), Y is O, L is —$CH_2$—, $R_2$ is H, $R_3$ is H, $Z_1$ is N, $Z_2$ is carbon, $Z_3$ is N, and X is OH (Compound 24), or a salt thereof.

In another embodiment, the monocotyledonous plant is rice, wheat, corn, barley, or sugarcane.

In a preferred embodiment, the plants are dicotyledonous and the compounds are of Formula I, wherein n is 1 or 2, when n is 1, $R_1$ is halogen, or lower alkoxy, and when n is 2, each $R_1$ is a halogen; L is —$CH_2$—, Y is S, $R_2$ is H, $R_3$ is H, $Z_1$ is N, $Z_2$ is carbon, $Z_3$ is N, and X is OH, or a salt thereof. In a more preferred embodiment, when n is 2, $R_1$ is in the 2,3-, 2,4-, 2,5-, 2,6-, 3,4- or 3,5-positions.

In a more preferred embodiment of the invention, the plants are dicotyledonous and the compounds are of Formula I where n is 1, $R_1$ is 3-F, L is —$CH_2$—, Y is S, $R_2$ is H, $R_3$ is H, $Z_1$ is N, $Z_2$ is carbon, $Z_3$ is N, and X is OH (Compound 1);

n is 0 ($R_1$ is absent), L is —$CH_2$—, Y is S, $R_2$ is H, $R_3$ is H, $Z_1$ is N, $Z_2$ is carbon, $Z_3$ is N, and X is OH (Compound 2);

n is 1, $R_1$ is 4-F, L is —$CH_2$—, Y is S, $R_2$ is H, $R_3$ is H, $Z_1$ is N, $Z_2$ is carbon, $Z_3$ is N, and X is OH (Compound 3);

n is 1, $R_1$ is 2-F, L is —$CH_2$—, Y is S, $R_2$ is H, $R_3$ is H, $Z_1$ is N, $Z_2$ is carbon, $Z_3$ is N, and X is OH (Compound 4);

n is 2, $R_1$ is 3,4-diF, L is —$CH_2$—, Y is S, $R_2$ is H, $R_3$ is H, $Z_1$ is N, $Z_2$ is carbon, $Z_3$ is N, and X is OH (Compound 5);

n is 2, $R_1$ is 3,5-diF, L is —$CH_2$—, Y is S, $R_2$ is H, $R_3$ is H, $Z_1$ is N, $Z_2$ is carbon, $Z_3$ is N, and X is OH (Compound 6);

n is 1, $R_1$ is 3-MeO, L is —$CH_2$—, Y is S, $R_2$ is H, $R_3$ is H, $Z_1$ is N, $Z_2$ is carbon, $Z_3$ is N, and X is OH (Compound 7), or n is 1, $R_1$ is 4-MeO, L is —$CH_2$—, Y is S, $R_2$ is H, $R_3$ is H, $Z_1$ is N, $Z_2$ is carbon, $Z_3$ is N, and X is OH (Compound 8), or a salt thereof.

In a preferred embodiment, the plants are dicotyledonous and the compounds are of Formula I where n is 1, $R_1$ is F, L is —$CH_2$—, Y is S, $R_2$ is H, $R_3$ is H, $Z_1$ is N, $Z_2$ is carbon, $Z_3$ is N, and X is OH, or a salt thereof.

In a more preferred embodiment, n is 1, $R_1$ is 3-F, L is —$CH_2$—, Y is S, $R_2$ is H, $R_3$ is H, $Z_1$ is N, $Z_2$ is carbon, $Z_3$ is N, and X is OH, or a salt thereof.

In another embodiment, the plants are dicotyledonous and the compounds are of Formula I where n is 0 and $R_1$ is absent, or n is 1 and $R_1$ is 3-F, 2-Cl, or 2-methyl, or n is 2 and $R_1$ is 2,6-diCl; L is —$CH_2$—; Y is S; $Z_1$ is N, and X is H or OH; or a salt thereof.

In a preferred embodiment, the plants are dicotyledonous and the compounds are of Formula I where n is 0 ($R_1$ is absent), $R_2$ is H, $R_3$ is OH, L is —$CH_2$—, Y is S, $Z_1$ is N, $Z_2$ is carbon, $Z_3$ is N, and X is OH (Compound 10);

n is 1, $R_1$ is 3-F, $R_2$ is H, $R_3$ is H, L is —$CH_2$—, Y is S, $Z_1$ is N, $Z_2$ is N, $Z_3$ is carbon, and X is OH (Compound 11);

n is 1, $R_1$ is 3-F, $R_2$ and $R_3$ taken together constitute a —N=CH—NH— bridge forming a ring, L is —$CH_2$—, Y is S, $Z_1$ is N, $Z_2$ is carbon, $Z_3$ is N, and X is OH (Compound 13);

n is 1, $R_1$ is 2-methyl, $R_2$ is H, $R_3$ is methyl, L is —$CH_2$—, Y is S, $Z_1$ is N, $Z_2$ is carbon, $Z_3$ is N, and X is OH (Compound 14);

n is 0 ($R_1$ is absent), $R_2$ is H, $R_3$ is H, L is —$CH_2$—, Y is S, $Z_1$ is N, $Z_2$ is carbon, $Z_3$ is N, and X is OH (Compound 15);

n is 2, $R_1$ is 2,6-diCl, $R_2$ is H, $R_3$ is methyl, L is —$CH_2$—, Y is S, $Z_1$ is N, $Z_2$ is carbon, $Z_3$ is N, and X is OH (Compound 16);

n is 1, $R_1$ is 3-F, $R_2$ is H, $R_3$ is H, L is —$CH_2$—, Y is S, $Z_1$ is N, $Z_2$ is carbon, $Z_3$ is N, and X is H (Compound 17);

n is 1, $R_1$ is 3-F, $R_2$ is H, $R_3$ is OH, L is —$CH_2$—, Y is S, $Z_1$ is N, $Z_2$ is carbon, and $Z_3$ is N, and X is OH (Compound 18); or n is 1, $R_1$ is 2-Cl, $R_2$ is H, $R_3$ is $CH_3$, L is —$CH_2$—, Y is S, $Z_1$ is N, $Z_2$ is carbon, $Z_3$ is N, and X is OH (Compound 20), or a salt thereof.

In yet another embodiment, the plants are dicotyledonous and the compounds are of Formula I where n is 0 and $R_1$ is absent, or n is 1 and $R_1$ is 3-F; $R_2$ is H, $R_3$ is H, $Z_1$ is N, $Z_2$ is carbon, $Z_3$ is N, and X is OH, or a salt thereof.

In a preferred embodiment, the plants are dicotyledonous and the compounds are of Formula I where n is 1, $R_1$ is 3-F, Y is O, L is —$CH_2$—, $R_2$ is H, $R_3$ is H, $Z_1$ is N, $Z_2$ is carbon, $Z_3$ is N, and X is OH (Compound 21);

n is 0 ($R_1$ is absent), Y is S, L is —$CH_2CH_2$—, $R_2$ is H, $R_3$ is H, $Z_1$ is N, $Z_2$ is carbon, $Z_3$ is N, and X is OH (Compound 22);

n is 0 ($R_1$ is absent), Y is S, L is —CH=$CHCH_2$—, $R_2$ is H, $R_3$ is H, $Z_1$ is N, $Z_2$ is carbon, $Z_3$ is N, and X is OH (Compound 23); or n is 0 ($R_1$ is absent), Y is O, L is —$CH_2$—, $R_2$ is H, $R_3$ is H, $Z_1$ is N, $Z_2$ is carbon, $Z_3$ is N, and X is OH (Compound 24), or a salt thereof.

In an embodiment, the dicotyledonous plant is mungbean, soybean, cotton, lettuce, tomato, rapeseed, radish, apple, grape, or peach.

In a further embodiment, the invention is directed to methods for enhancing monocotyledonous or dicotyledonous plant growth comprising applying the S-Benzylthiouracil compounds of Formula I, wherein n is 1, $R_1$ is 3-F, L is —$CH_2$—, Y is S, $R_2$ is H, $R_3$ is H, $Z_1$ is N, $Z_2$ is carbon, $Z_3$ is N, and X is OH (Compound 1), or a potassium salt thereof, to a plant, plant propagation material, root zone, or root of a plant.

In another embodiment, the invention is directed to methods for reducing the harmful effects of drought or high or low temperatures comprising applying the S-Benzylthiouracil compounds of Formula I, wherein n is 1, $R_1$ is 3-F, L is —$CH_2$—, Y is S, $R_2$ is H, $R_3$ is H, $Z_1$ is N, $Z_2$ is carbon, $Z_3$ is N, and X is OH (Compound 1), or a salt thereof, to a plant, plant propagation material, root zone, or root of a plant.

In yet another embodiment, the invention is directed to S-Benzylthiouracil derivatives. These derivatives are compounds of Formula I, wherein n is 2, $R_1$ is 3,4-diF, L is —$CH_2$—, Y is S, $R_2$ is H, $R_3$ is H, $Z_1$ is N, $Z_2$ is carbon, $Z_3$ is N, and X is OH (Compound 5);

n is 2, $R_1$ is 3,5-diF, L is —$CH_2$—, Y is S, $R_2$ is H, $R_3$ is H, $Z_1$ is N, $Z_2$ is carbon, $Z_3$ is N, and X is OH (Compound 6);

n is 1, $R_1$ is 3-F, $R_2$ is —COO-ethyl, L is —$CH_2$—, Y is S, $Z_1$ is N, $Z_2$ is carbon, $Z_3$ is N, and X is OH (Compound 12);

n is 1, $R_1$ is 2-methyl, $R_2$ is H, $R_3$ is methyl, L is —$CH_2$—, Y is S, $Z_1$ is N, $Z_2$ is carbon, $Z_3$ is N, and X is OH (Compound 14);

n is 2, $R_1$ is 2,6-diCl, $R_2$ is H, $R_3$ is methyl, L is —$CH_2$—, Y is S, $Z_1$ is N, $Z_2$ is carbon, $Z_3$ is N, and X is OH (Compound 16);

n is 1, $R_1$ is 3-F, $R_2$ is H, $R_3$ is H, L is —$CH_2$—, Y is S, $Z_1$ is N, $Z_2$ is carbon, $Z_3$ is N, and X is $NH_2$ (Compound 19);

n is 1, $R_1$ is 3-F, Y is O, L is —$CH_2$—, $R_2$ is H, $R_3$ is H, $Z_1$ is N, $Z_2$ is carbon, $Z_3$ is N, and X is OH (Compound 21); or n is 0 ($R_1$ is absent), Y is O, L is —$CH_2$—, $R_2$ is H, $R_3$ is H, $Z_1$ is N, $Z_2$ is carbon, $Z_3$ is N, and X is OH (Compound 24), or a salt thereof.

The disclosed embodiments are simply exemplary embodiments of the inventive concepts disclosed herein and should not be considered as limiting, unless the claims expressly state otherwise.

As used herein "salts" refers to those salts which retain the biological effectiveness and properties of the parent compounds and which are not biologically or otherwise harmful at the dosage administered. Salts of the compounds of the present inventions may be prepared from inorganic or organic acids or bases.

Examples of such inorganic salts include calcium, magnesium, potassium, sodium and ammonium salts. Typical examples of organic salts include trimethylammonium salt, isopropylammonium salt, 2-hydroxyethylammonium salt (ethanolamine salt), 2-hydroxyethyldimethylammonium salt (dimethylethanolamine salt), bis(2-hydroxyethyl)ammonium salt (diethanolamine salt), tris(2-hydroxyethyl)ammonium salt (triethanolamine salt), the 2-hydroxyethyltrimethylammonium salt (choline salt) and the tetramethylguanidinium salt. The preferred salt is the sodium salt.

When salts of the present invention are made, the compounds are of Formula I wherein X is —$O^-$, associated with a cation chosen from $Na^+$, $K^+$, tetramethylguanidium$^+$, choline$^+$, or $(R)_4N^+$, where R is lower alkyl.

The salts of S-Benzylthiouracil compounds are produced, for example, by suspending the neutral S-Benzylthiouracil compounds in water and adding an equimolar amount of a base to the suspension. In the case of the sodium salt, sodium hydroxide is preferably used as the base and this method allows for the production of sodium salt solutions comprising from 0.1 to 40% of the S-Benzylthiouracil compound. Further details on how to prepare salts of the present invention are in Example 2 below.

Compositions Containing S-Benzylthiouracil Compounds

The compositions of the present invention further comprise a carrier in general, and optionally auxiliaries for formulation. Examples of auxiliaries include surfactants, dispersing agents, thickeners, stabilizing agents, antifreezing agents and colorants.

Examples of solid carriers include powders and granules of clays such as kaolin clay, diatomaceous earth, bentonite, fubasami clay and terra alba; synthetic hydrated silica; talc; ceramic; other inorganic minerals such as sericite, quartz, sulfur, activated carbon, calcium carbonate and hydrated silica; and chemical fertilizers such as ammonium sulfate, ammonium phosphate, ammonium nitrate, ammonium chloride and urea. When the composition contains a solid carrier, the amount of the carrier is usually 1 to 99% by weight of the composition.

Examples of liquid carriers include aromatic and aliphatic hydrocarbons such as xylene, toluene, alkylnaphthalene, phenylxylylethane, kerosene, gas oil, hexane and cyclohexane; halogenated hydrocarbons such as chlorobenzene, dichloromethane, dichloroethane and trichloroethane; alcohols such as methanol, ethanol, isopropyl alcohol, butanol, hexanol, benzyl alcohol and ethylene glycol; ethers such as ethylene glycol monoethyl ether, diethylene glycol monomethyl ether, diethylene glycol monoethyl ether, propylene glycol monomethyl ether, tetrahydrofuran and dioxane; esters such as ethyl acetate and butyl acetate; ketones such as acetone, methyl ethyl ketone, methyl isobutyl ketone and cyclohexanone; nitriles such as acetonitrlile and isobutyronitrile; sulfoxides such as dimethyl sulfoxide (DMSO); amides such as N,N-dimethylformamide, N,N-dimethylacetamide and N-methylpyrolidinone; alkylydene carbonates such as ethylene carbonate, propylene carbonate; vegetable oils such as soybean oil and cotton seed oil; plant essential oils such as orange oil, hyssop oil and lemon oil; and water. When the composition contains a liquid carrier, the amount of the carrier is usually from about 1 to about 99% by weight of the composition.

Examples of gaseous carriers include butane gas, freon gas, liquefied petroleum gas (LPG), dimethyl ether and carbon dioxide. When the composition contains a gaseous carrier, the amount of the carrier is usually 1 to 99% by weight of the composition.

Examples of surfactants include alkylsulfate salts, alkylsulfonate salts, alkylarylsulfonate salts such as alkylbenzenesulfonate salts and alkylnaphthalenesulfonate salts, polyoxyethylene alkyl ether phosphate salts, alkylaryl ethers, polyoxyethylene alkylaryl ethers, polyethylene glycol ethers, polyvalent alcohol esters and sugar alcohols.

Examples of dispersing agents include calcium ligninsulfonate, methylcellulose and hydroxymethylcellulose.

Examples of thickeners include aluminum magnesium silicate, gum arabic, polyvinyl alcohol and polyvinylpyrrolidinone.

Examples of stabilizing agents include BHT (2,6-di-tert-butyl-4-methylphenol) and BHA (mixture of 2-tert-butyl-4-methoxyphenol and 3-tert-butyl-4-methoxyphenol).

Examples of antifreezing agents include ethylene glycol, propylene glycol, trimethylene glycol, 1,2-butanediol, 1,3-butanediol, 1,4-butanediol, 1,4-pentanediol, 3-methyl-1,5-pentanediol, 2,3-dimethyl-2,3-butanediol, trimethylol propane, mannitol, sorbitol, glycerol, pentaerythritol, 1,4-cyclohexanedimethanol, xylenol, bisphenols such as bisphenol A or the like, diethylene glycol, triethylene glycol, tetraethylene glycol, polyoxyethylene or polyoxypropylene glycols of molecular weight up to about 4000, diethylene glycol monomethyl ether, diethylene glycol monoethyl ether, triethylene glycol monomethyl ether, butoxyethanol, butylene glycol monobutyl ether, dipentaerythritol, tripentaerythritol, tetrapentaerythritol, diglycerol, triglycerol, tetraglycerol, pentaglycerol, hexaglycerol, heptaglycerol and octaglycerol.

Examples of colorants include azo dyestuffs and anthraquinone dyestuffs. When the composition contains a colorant, the amount of the colorant is usually 0.01 to 1.0% by weight in the composition.

The composition of the present invention is prepared by conventional methods, for example, by mixing the S-Benzylthiouracil compound or a salt thereof, a carrier and optionally auxiliaries, and further pulverization, granulation, or other means to make a uniform formulation. The composition of the present invention can be a variety of formulations: dry flowables (DF), liquid flowables (LF), true liquids (TL), emulsifiable concentrates (EC), dusts (D), wettable powders (WP), suspoemulsions (SE), water-dispersible granules (WG) and others.

The concentration of the S-Benzylthiouracil compound, or a salt thereof, is from 0.01 to 99.9 percent by weight of the composition.

The application dosage of the composition of the present invention is usually from about 0.0001 to about 10.0 mg/seed, preferably from about 0.01 to about 1 mg/seed of the amount of the S-Benzylthiouracil compound, or salt thereof.

DEFINITIONS

As used herein, "alkyl" refers to a straight or branched chain or cyclic alkane radical (i.e. a group missing one of the hydrogen atoms required for a stable structure, having a general formula $—C_nH_{2n+1}$ for straight or branched chain alkyl or $—C_nH_{2n-1}$ for cyclic alkyl). Examples of alkyls include methyl, ethyl, propyl, iso-propyl, cyclopropyl, butyl, sec-butyl, pentyl, and hexyl. A "lower alkyl" thus refers to any such alkyl containing 1 to 6 carbons.

As used herein, "lower alkoxy" refers to a lower alkyl group connected through an ether oxygen. Examples of lower alkoxy groups include methoxy, ethoxy, propoxy, iso-propoxy, butoxy, sec-butoxy, cyclobutoxy, pentoxy, and hexyloxy. A lower alkoxy group thus refers to any such alkoxy group containing 1 to 6 carbons.

The term "halogen," as used herein, refers to fluorine, chlorine, bromine and iodine.

As used herein, "plants" refers to plants with roots, including both monocotyledonous and dicotyledonous plants.

Monocotyledonous plants suitable for use with methods of the present invention include, but are not limited to, corn (maize), barley, wheat, rice and sugarcane.

Dicotyledonous suitable for use with methods of the present invention include, but are not limited to, mungbean, soybean, cotton, lettuce, tomato, rapeseed (canola), radish, and perennial plants such as apple, grape and peach.

As used herein, the phrase "enhancing root growth" refers to an improvement in root growth compared to untreated plants. For example, an increase in the primary root length, an increase in the total root mass, an increase in the average length of roots, an increase in the average thickness of roots, an increase in the speed of root growth, and an increase in the number of secondary roots would all be considered an enhancement of the plant's root growth.

The methods of the present invention may be used on plants including genetically-modified or non-genetically-modified, or wild type, plants.

As used herein, "root zone" refers to the area in the vicinity of the plant where a compound can be taken up by the plant roots. In the case of many plants, this is considered to be within the drip line, where a spray to the aerial part of a plant would not drip directly to the soil, but would be blocked by the foliage.

As used herein, the phrase "plant propagation material" refers to seeds, cuttings, corms, tubers, cells or other materials from which a plant may be regenerated or grown. This phrase is not limited to seeds or fruits, but may include materials that are used for asexually propagating crops.

As used herein, "environmentally stressful conditions" are conditions in which the plant has limited access to at least one essential nutrient or water, or is exposed to temperatures that decrease or cause cell function to cease entirely.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The articles "a," "an" and "the" are intended to include the plural as well as the singular, unless the context clearly indicates otherwise.

The following examples are intended to illustrate the present invention and to teach one of ordinary skill in the art how to use the formulations of the invention. They are not intended to be limiting in any way.

EXAMPLES

Example 1

Synthesis of Novel S-Benzylthiouracil Compounds

The S-Benzylthiouracil compounds of the present invention were synthesized by standard methods. Structural confirmation and purity determinations were performed by HPLC with electrospray mass spectrometry. The following methods were used to create the novel compounds of the present invention.

Synthesis of S-(3,4-Difluorobenzyl)-2-thiouracil (Compound 5)

This compound was prepared by reaction in 5 mL of anhydrous dimethylformamide, reacting 1.28 g (10 mmol) of 2-thiouracil with 2.07 g of alpha-bromo-3,4-difluorotoluene (10 mmol), stirring at ambient temperature overnight. The reaction mixture was quenched by adding it dropwise, with rapid stirring, to 25 mL of 0.5 M aqueous $NaHCO_3$. The product was collected by filtration, washed with a small volume of water and dried under vacuum. Yield was 2.22 g of Compound 5, a white powder, 95.5% pure by HPLC-electrospray MS, which confirmed the molecular weight of 254.

Synthesis of S-(3,5-Difluorobenzyl)-2-thiouracil (Compound 6)

A mixture of 512 mg of 2-thiouracil (4 mmol) and 828 mg of alpha-bromo-3,5-difluororotoluene (4 mmol) in 2 mL of anhydrous dimethylformamide was stirred at ambient temperature for 20 hours, giving a clear, colorless solution. The reaction was quenched by adding dropwise with good stirring to 10 mL of 0.5 M aqueous $NaHCO_3$. The product was collected by filtration, washed with a small volume of water and dried under vacuum. Yield was 917 mg of Compound 6, a white powder, 97% pure by HPLC-electrospray MS, which confirmed the molecular weight of 254.

Synthesis of S-(3-Fluorobenzyl)-5-carboxyethyl-2-thiouracil (Compound 12)

A mixture of 1.89 g of 3-fluorobenzyl bromide (10 mmol) and 2.00 g of ethyl 2-thiouracil-5-carboxylate (10 mmol) in 5 mL of anhydrous dimethylformamide was stirred at ambient temperature for seven days. The reaction was quenched by transferring it dropwise into a well-stirred solution of 810 microliters of pyridine (10 mmol) in 20 mL of water. The product was collected by filtration, rinsed with about 25 mL of water and dried under vacuum. Yield was 2.22 g of Compound 12, a white powder, 96.6% pure by HPLC-electrospray MS, which confirmed the molecular weight of 308.

Synthesis of S-(3-Fluorobenzyl)-6-methyl-2-thiouracil (Compound 14)

A mixture of 945 mg of 3-fluorobenzyl bromide (5 mmol) and 841 mg of 2-thio-6-hydroxypurine (5 mmol) was stirred at ambient temperature in 2.5 mL of anhydrous dimethylformamide. The reaction mixture solidified after approximately 3 hr, but the mixture was allowed to stand overnight before product recovery. The material was suspended in 25 mL of 0.5 M aqueous $NaHCO_3$. The product was collected by filtration, washed with 25 mL of water and dried under vacuum. Yield was 1.34 g of Compound 14, a pale yellow powder, 97.8% pure by HPLC-electrospray MS, which confirmed the molecular weight of 277.

Synthesis of S-(2,6-Dichlorobenzyl)-6-methyl-2-thiouracil (Compound 16)

A mixture of 1.42 g of 4-hydroxy-2-mercapto-6-methylpyrimidine (10 mmol) and 2.40 g of 2,6-dichlorobenzyl bromide (10 mmol) in 6 mL of anhydrous dimethylformamide was stirred at ambient temperature for six days. The reaction was quenched by transferring it dropwise into 10 mL of 1.0 M aqueous $NaHCO_3$ with good stirring. The product was collected by filtration, rinsed with about 10 mL of water and dried under vacuum. Yield was 2.22 g of Compound 16, a white powder, 95.5% pure by HPLC-electrospray MS, which confirmed the molecular weight of 301.

Synthesis of 3-F benzyl Substituted and 2-S4-=NH Uracil Substituted S-Benzylthiouracil (Compound 19)

A solution of 2.04 g 3-fluorobenzyl bromide (10.8 mmol) and 770 microliters of trifluoroacetic acid (10 mmol) was stirred while adding 1.27 g of 2-thiocytosine (10 mmol) in portions over several minutes. Stirring was continued overnight. The reaction was quenched by transferring dropwise into a well-stirred solution of 20 mmol of trimethylamine in 20 mL of water. The product initially separated as a gum, then it abruptly crystallized. The crystalline material was collected by filtration, washed with water and dried under vacuum. Yield was 937 mg of Compound 19, a white powder, 96.7% pure by HPLC-electrospray MS, which confirmed the molecular weight of 235.

Synthesis of 2-O-(3-fluorobenzyl)uracil (Compound 21)

Uracil (1.12 g, 10 mmol), 3-fluorobenzyl bromide (3.78 g, 20 mmol) and potassium carbonate (2.76 g, 20 mmol) were stirred in 7.5 mL of anhydrous DMF at ambient temperature for 4 days. The reaction was quenched by addition to 20 mL of water containing 1.20 g of acetic acid (20 mmol). The solid collected by filtration and air dried contained unreacted uracil in addition to the product. Trituration with a mixture of cyclohexane and methylene chloride extracted relatively pure product, Compound 21, with molecular weight 220 confirmed by HPLC-electrospray MS.

Synthesis of 2-O-Benzyluracil (Compound 24)

Uracil (1.12 g, 10 mmol) was dissolved in 12 mL water containing 529 microliters of 50% sodium hydroxide (10 mmol) with warming. The solution was allowed to cool to ca. 45° C., and 2 mL of methanol and 1.19 mL of benzyl bromide (10 mmol) were added. The mixture was stirred without heating for five days, at which point a substantial amount of a white gum has deposited out of solution. The liquid phase was decanted, and the residue was rinsed with 3 mL of 1.0 M aqueous NaOH. The residue was then triturated with two 10 mL portions of acetonitrile, keeping them separate. Removal of the solvent from the second acetonitrile wash left 133 mg of white powder, identified as Compound 24, 90% pure by HPLC-electrospray MS, which confirmed the molecular weight of 202.

Other S-Benzylthiouracil compounds can be synthesized using similar techniques. These techniques are known by those of skill in the art.

Example 2

Synthesis of Salts of S-Benzylthiouracil Compounds

The salts of the S-Benzylthiouracil compounds of the present invention were synthesized by standard methods. Structural confirmation and purity determinations were performed by HPLC with electrospray mass spectrometry. The following methods were used to create the salts of the compounds of the present invention.

Synthesis of the Potassium Salt of S-(3-Fluorobenzyl)-2-thiouracil (Compound 1)

S-(3-Fluorobenzyl)-2-thiouracil (Compound 1, 2.36 g, 10 mmol) was suspended in 23 mL of water and stirred well at ambient temperature while 10.0 mL of 1.0 M aqueous potassium hydroxide solution (10 mmol) was added over a period of about one minute. The white solid slowly dissolved almost completely. The final pH was 10.2. The solution was filtered into a tared flask, frozen into a shell inside the flask by rotating while chilling, and the water was removed by lyophilization. The product (the potassium salt of Compound 1) was a freely-flowing white powder weighing 2.69 g, with the chemical structure shown below.

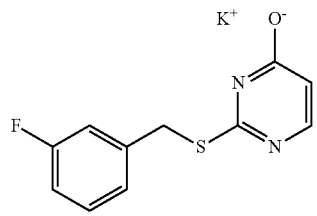 [SMILES: [O-]c1ccnc(SCc2cccc(F)c2)n1 ; [K+]]

Synthesis of the Sodium Salt of S-Benzyl-2-thiouracil (Compound 2)

Powdered S-Benzyl-2-thiouracil (2.18 g, 10 mmol) was suspended in 23 mL of water at ambient temperature with good stirring while 10.0 mL of 1.0 M aqueous sodium hydroxide solution (10 mmol) was added over a period of about 1 minute. Stirring was continued, and after one hour only a very small amount of fine white powder remained undissolved. The pH of the solution was 10.1. The mixture was filtered under vacuum through a pad of Celite ca. 5 mm thick into a tared flask. The solution was frozen into a shell inside the flask by rotating while chilling, and the water was removed by lyophilization. The product (the sodium salt of Compound 2) was a fluffy white powder with the chemical structure shown below.

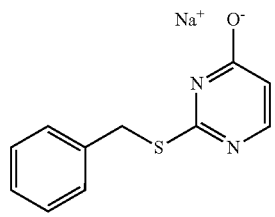 [SMILES: [O-]c1ccnc(SCc2ccccc2)n1 ; [Na+]]

Assay Procedures Explanations
Pouch Assay:

Seeds were placed in germination pouches consisting of germination paper as an insert in a gas-permeable 16×14 cm plastic pouch (CYG Pouch; Mega International, St. Paul, Minn.). In pouch solution evaluation, S-Benzylthiouracil compounds or their salts were dissolved in a small volume of DMSO and added to sterile water with a maximum of 0.5% v/v DMSO at final dilution. The S-Benzylthiouracil solution was subsequently pipetted into the growth pouch, followed by the addition of seeds of the crop being tested. The pouches were arranged in a randomized complete block design in growth racks and placed in 19-liter polycarbonate food storage containers (Rubbermaid Commercial Products, Winchester, Va.). The sealed containers were held in an upright growth cabinet maintained at 25 C with a 12 hour light: 12 hour dark photoperiod. For rice, plants were harvested at 6 d, while in mungbean and corn, the plants were harvested at 4 d post sowing. Measurements were performed on the primary root and shoot of each seedling.

Petri Plate Assays:

For tomato, the plants were grown in disposable (150 mm) sterile plastic petri plates (Falcon, BD Biosciences, Franklin Lakes, N.J.). In the tomato assay, a single sheet of Whatman #1 filter paper was placed at the bottom of the plate, 15 tomato seeds were added, and 10 mL of treatment solution was added. At the end of 6 d, the 10 largest seedlings were selected for measurement from each plate. In each study, a minimum of 3 replicate plates were used.

For *Arabidopsis*, a solid medium was required. Typically, half-strength MS salts were dissolved in water, and 1% (w/v) BactoAgar (DIFCO) was added. Following autoclaving, sterile S-Benzylthiouracil solutions were added to medium prior to pouring 30 mL of agar medium per petri plate. *Arabidopsis* seeds were sown in a sterile manner, and seeds were germinated and grew on the agar surface until primary root length was measured.

Seed Treatment Assays:

Seed was sieved with a screen of mesh size appropriate to remove broken seeds and small trash. Cracked or otherwise damaged seeds were removed. The seed was mixed well, and 50 g samples were weighed into small plastic trays. Seed treatment slurries were made by adding measured amounts of the S-Benzylthiouracil compounds or salts thereof under test and other conventional seed treating components to sufficient water to bring them up to a standard volume, typically 2 mL. A fungicide (Maxim XL; Syngenta Agricultural Products, Greensboro, N.C.), a polymeric binder (CF-Clear; Becker-Underwood, Ames, Iowa), and a colorant (Color Coat Red; Becker-Underwood, Ames, Iowa) were also included in the slurry at label rates. A small aliquot of this slurry was applied to the seed using the Hege 11 coater (Wintersteiger, Salt Lake City, Utah) with a six-inch bowl at a slurry rate of 30 ounces per 100 pounds of seed. The slurry was deposited dropwise on the spinning disk atomizer using a syringe.

After treatment, each seed sample was placed in a plastic tray and dried at room temperature for 20 to 60 minutes. The samples were then placed in small plastic bags.

Stress Studies

Drought Stress:

Germinated rice seeds (cultivar; Nipponbare) were cultivated in 2-fold diluted Kimura B hydroponic solution in a growth chamber at a temperature of 28° C. (day)/23° C. (night) and a day length of 12 hours for 14 days. Drought stress was provided by withdrawal of the hydroponic solution from the culture tube for 2 days in a growth chamber at a temperature of 28° C. (day)/23° C. (night) and a day length of 12 hours. After the drought treatment, plants were cultivated in 2-fold diluted Hoagland's hydroponic solution in a growth chamber at a temperature of 28° C. (day)/23° C. (night)) and a day length of 12 hours for 14 days. Then the total fresh weight of the shoots of 5 plants was measured for 3 replicates.

Foliar Applications:

Wheat (cultivar; Apogee) was sown in soil pots (5 seeds/pot) and then cultivated in a growth chamber at a temperature of 18° C. (day)/15° C. (night) and at a day length of 12 hours for 28 days. Plants were thinned to 3 plants/pot. On the 28th day after sowing, the plants were treated by foliar spray application with a solution containing the test compound. On the 2nd day after the spray application the plants were subjected to high temperatures for 7 days in a growth chamber 36° C. (day)/32° C. (night) and a day length of 12 hours. After the stress treatment, the plants were cultivated in a growth chamber at a temperature of 18° C. (day)/15° C. (night) and a day length of 12 hours. On the 56th day after seeding, the total fresh weight of the young ears from the 3 plants in each pot was measured (n=8 replicates).

Example 3

Rice Pouch Assay

The growth of the primary root of rice was examined in the pouch assay system. The results of the testing, presented as percent change in root length across all S-Benzylthiouracil compounds, are shown below.

S-Benzylthiouracil analogs and derivatives are described in the following tables (1-3). In Table 1, the S-Benzylthiouracil compounds with substitutions on the benzyl ring are examined. The activities of these compounds as a percent increase as compared to the control, for the root growth of rice are presented.

TABLE 1

The Effect of S-Benzylthiouracil Compounds with Substitutions on the Benzyl Ring on Rice Root Growth (concentrations were 10 ppm (10 mg/L))

| Compound Number | Structure | Benzyl Substitution | Percent Change in Primary Root Length in Rice |
|---|---|---|---|
| 1 | (structure shown) | 3-F | 19.8 |
| 2 | (structure shown) | None = S-Benzylthiouracil | 15.6 |

TABLE 1-continued

The Effect of S-Benzylthiouracil Compounds with Substitutions on the
Benzyl Ring on Rice Root Growth (concentrations were 10 ppm (10 mg/L))

| Compound Number | Structure | Benzyl Substitution | Percent Change in Primary Root Length in Rice |
|---|---|---|---|
| 3 | 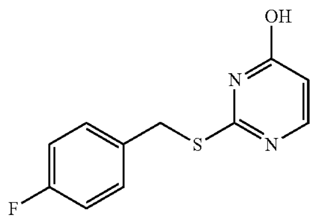 [SMILES: Oc1ccnc(SCc2ccc(F)cc2)n1] | 4-F | 13.9 |
| 4 | 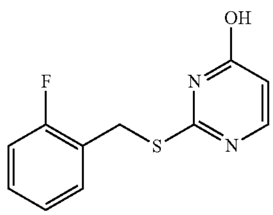 [SMILES: Oc1ccnc(SCc2ccccc2F)n1] | 2-F | 13.5 |
| 5 | 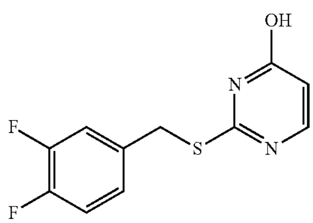 [SMILES: Oc1ccnc(SCc2ccc(F)c(F)c2)n1] | 3,4-DiF | 13.4 |
| 6 | 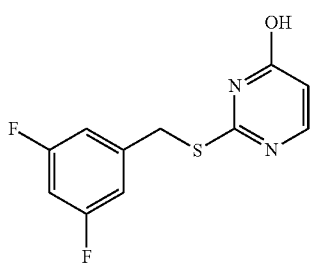 [SMILES: Oc1ccnc(SCc2cc(F)cc(F)c2)n1] | 3,5-DiF | 8.8 |
| 7 | 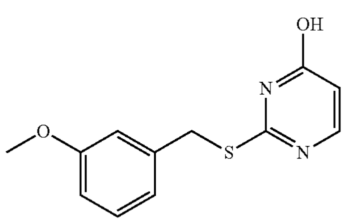 [SMILES: COc1cccc(CSc2nccc(O)n2)c1] | 3-MeO | 2.5 |
| 8 | 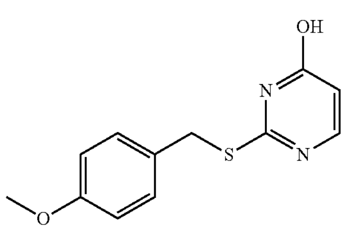 [SMILES: COc1ccc(CSc2nccc(O)n2)cc1] | 4-MeO | 0.4 |

TABLE 1-continued

The Effect of S-Benzylthiouracil Compounds with Substitutions on the
Benzyl Ring on Rice Root Growth (concentrations were 10 ppm (10 mg/L))

| Compound Number | Structure | Benzyl Substitution | Percent Change in Primary Root Length in Rice |
|---|---|---|---|
| 9 | [structure] | 3-Me | −2.3 |

Table 1 shows that the activity of the S-Benzylthiouracil compounds on rice root growth is greatest when S-Benzylthiouracil is either substituted with a halogen in the meta or para position, or is unsubstituted.

In Table 2, S-Benzylthiouracil compounds with modifications of the uracil moiety are shown, as well as their root growth promoting activity.

TABLE 2

The Effect of S-Benzylthiouracil Compounds with Substitutions of the
Uracil Moiety on Rice Root Growth (concentrations were 10 ppm (10 mg/L))

| Compound Number | Structure | Benzyl Substitution | Uracil Substitution | Percent Change in Primary Root Length in Rice |
|---|---|---|---|---|
| 10 | [structure] | None | 2-S 6-OH | 11.5 |
| 11 | [structure] | 3-F | 4-S | 10.6 |
| 12 | [structure] | 3-F | 2-S-5-COOEt | 9.5 |
| 13 | [structure] | 3-F | 2-S-5,6-imidazole | 8.7 |

TABLE 2-continued

The Effect of S-Benzylthiouracil Compounds with Substitutions of the
Uracil Moiety on Rice Root Growth (concentrations were 10 ppm (10 mg/L))

| Compound Number | Structure | Benzyl Substitution | Uracil Substitution | Percent Change in Primary Root Length in Rice |
|---|---|---|---|---|
| 14 | 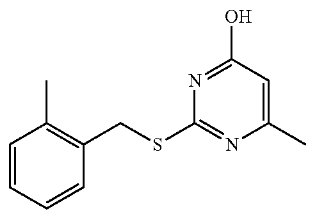 [SMILES: Cc1cc(O)nc(SCc2ccccc2C)n1] | 2-Methyl | 2-S-6-Me | 8.6 |
| 15 | 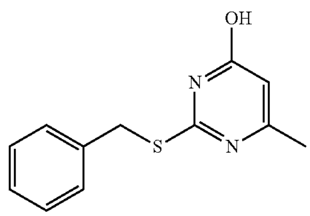 [SMILES: Cc1cc(O)nc(SCc2ccccc2)n1] | None | 2-S-6-Me | 7.6 |
| 16 | 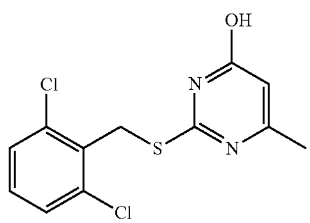 [SMILES: Cc1cc(O)nc(SCc2c(Cl)cccc2Cl)n1] | 2,6-DiCl | 2-S-6-Me | 5.5 |
| 17 | 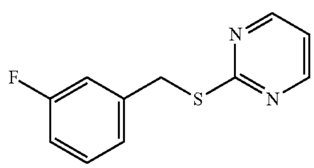 [SMILES: Fc1cccc(CSc2ncccn2)c1] | 3-F | X = H | 5.1 |
| 18 | 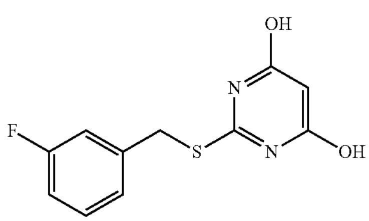 [SMILES: Oc1cc(O)nc(SCc2cccc(F)c2)n1] | 3-F | 2-S-6-OH | 4.0 |
| 19 | 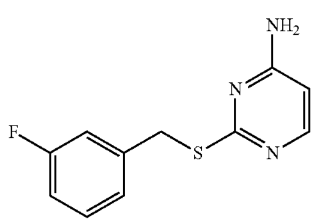 [SMILES: Nc1ccnc(SCc2cccc(F)c2)n1] | 3-F | 2-S-4-$NH_2$ | 2.9 |
| 20 | 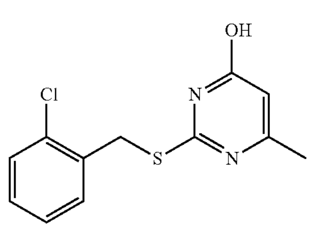 [SMILES: Cc1cc(O)nc(SCc2ccccc2Cl)n1] | 2-Cl | 2-S-6-Me | −6.9 |

Substitutions to the uracil moiety generally showed some root enhancement in rice. The only significantly negative effect on root growth enhancement was observed with a combination of 2-Cl on the benzyl ring combined with methylation of the uracil moiety at the 6-position (Compound 20). This negative activity was not expected, because Compound 15 has the same uracil substitution and still provided an increase in root growth of 7.6 percent.

S-Benzylthiouracil compounds with changes in the linkage between the benzyl ring and uracil moiety were also tested to determine the root enhancement effect in rice. The results are below in Table 3.

TABLE 3

The Effect of S-Benzylthiouracil Compounds with Changes to the Linkage Between the Benzyl Ring and Uracil Moieties on Rice Root Growth (concentrations were 10 ppm (10 mg/L))

| Compound Number | Structure | Benzyl Sub. | Link | Uracil Sub. | Percent Change in Primary Root Length of Rice |
|---|---|---|---|---|---|
| 21 | 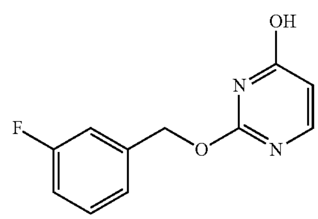 [SMILES: Oc1ccnc(OCc2cccc(F)c2)n1] | 3-F | —CH$_2$O— | 2-O | 6.0 |
| 22 | 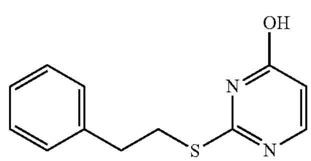 [SMILES: Oc1ccnc(SCCc2ccccc2)n1] | None | —CH$_2$CH$_2$S— | 2-S | 5.3 |
| 23 | 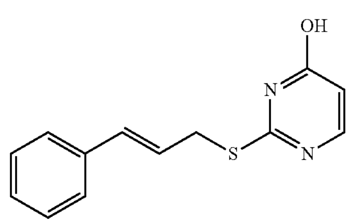 [SMILES: Oc1ccnc(SC/C=C/c2ccccc2)n1] | None | —CH=CHCH$_2$S— | 2-S | 2.3 |
| 24 | 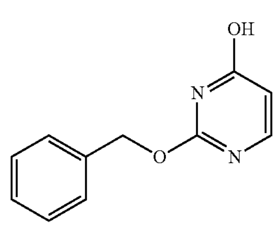 [SMILES: Oc1ccnc(OCc2ccccc2)n1] | None | —CH$_2$O— | 2-O | 2.2 |

When compounds with a change to the linkage ("X" in structure) of the S-Benzylthioracil compounds were applied to rice, they provided modest enhancements to root growth. As compared to the parent molecules, substitution of the sulfur with an oxygen (in Compounds 21 and 24) reduced root growth promoting activity by greater than 66 percent. Increasing the chain length of the linkage or insertion of a double bond in the linkage group provided modest enhancements in root growth (Compounds 22 and 23).

In Table 4 below, the actual root lengths induced by Compound 2 are shown.

TABLE 4

The Effect of Compound 2 on Rice Root Growth at 6 Days After Treatment

| Compound ppm | Root Length (cm) |
| --- | --- |
| 0 (untreated control) | 5.7 |
| 1 | 6.7 |
| 10 | 7.8 |

Table 4 shows that Compound 2 increased the root length compared to the control treatment.

Similarly, Table 5 shows the root lengths induced by Compound 1, which on average resulted in the greatest increases in root length compared to all of the other tested compounds.

TABLE 5

The Effect of Compound 1 on Rice Root and Shoot Growth at 6 Days After Treatment

| Concentration ppm | Root Length (cm) | Shoot Length (cm) |
| --- | --- | --- |
| 0 (untreated control) | 5.1 | 1.7 |
| 7.5 | 7.8 | 2.2 |
| 30 | 7.3 | 2.2 |
| 100 | 5.2 | 1.9 |

In Table 6, a dose-dependent increase in root length was shown by continuous treatment with Compound 1. Not all S-Benzylthiouracil compounds resulted in increased root growth in rice. In Table 5, the results observed with Compound 20 are shown.

TABLE 6

The Effect of Compound 20 on Rice Root and Shoot Growth at 6 Days After Planting

| Compound ppm | Root Length (cm) | Shoot Length (cm) |
| --- | --- | --- |
| 0 | 5.4 | 1.7 |
| 1 | 5.3 | 1.4 |
| 2 | 4.7 | 1.3 |
| 5 | 4.6 | 1.2 |
| 10 | 3.8 | 0.9 |

The effect the S-Benzylthiouracil compounds would have on the root growth on rice was unpredictable. Table 6 shows that unlike the other S-Benzylthiouracil compounds, Compound 20 showed dose-dependent reductions in root and shoot growth. Some compounds showed increased root growth, while others hindered the root growth compared to the control. It was unexpected that Compound 1 had such a positive effect on rice root growth.

A significant practical limitation of the utility of the S-Benzylthiouracil compounds as root growth promoters is their relative insolubility in water. One means of increasing the solubility of the S-Benzylthiouracil compounds is to convert them to water-soluble salts, which are ionized in aqueous media. In the case of the S-Benzylthiouracil compounds, the base molecule is the anion, which may be produced with a variety of cations. The choice of cation may affect the uptake and activity of the S-Benzylthiouracil compounds. A table of water-soluble salts tested and their activity, a percent change in rice root length, is shown in Table 7 below.

TABLE 7

The Effect of 10 ppm S-Benzylthiouracil Compounds and Their Water-Soluble Salts on Rice Primary Root Growth at 6 Days After Sowing

| Base Compound | Salt | Percent Change |
| --- | --- | --- |
| Control | | 0.0 |
| Compound 2 | None | 15.6 |
| Compound 2 | Potassium | 10.5 |
| Compound 2 | Choline | 5.3 |
| Compound 2 | Tetramethylguanidine | 11.8 |
| Compound 1 | None | 19.8 |
| Compound 1 | Tetramethylguanidine | -1.8 |
| Compound 1 | Sodium | 15.5 |
| Compound 18 | None | 4.0 |
| Compound 18 | Sodium | -0.2 |

A comparative study of selected S-Benzylthiouracil compounds and their salts is shown below in Table 8.

TABLE 8

The Effect of S-Benzylthiouracil Compounds or S-Benzylthiouracil Salts at 10 ppm Equivalent on Primary Root Growth of Rice at 6 Days After Sowing

| Compound | Root Length (cm) | Shoot Length (cm) |
| --- | --- | --- |
| Control | 8.61 | 2.96 |
| Compound 3 | 9.38 | 2.59 |
| Compound 3, K salt | 9.42 | 2.68 |
| Compound 3, Choline salt | 8.43 | 2.82 |
| Compound 3, Tetramethylguanidine salt | 9.68 | 2.85 |
| Compound 16 | 9.31 | 2.71 |
| Compound 16, Tetramethylguanidine salt | 7.74 | 2.58 |

A more systematic study of salts of compounds 1 and 2 is shown below in Tables 9 and 10, respectively

TABLE 9

The Effect of K+ salt of Compound 1 on Rice Root Growth 6 Days After Sowing

| | Root Length (cm) | |
| --- | --- | --- |
| Concentration (mg/liter) | Compound 1 | Compound 1 K+ salt |
| 0 (Untreated control) | 9.67 | |
| 10 mg/liter | 10.80 | 11.03 |
| 30 mg/liter | 10.34 | 9.71 |

TABLE 10

The Effect of Na+ salt of Compound 2
on Rice Root Growth 6 Days After Sowing

| Concentration (mg/liter) | Root Length (cm) | |
|---|---|---|
| | Compound 2 | Compound 2 Na+ salt |
| 0 (Untreated control) | 10.50 | |
| 10 mg/liter | 12.44 | 12.35 |
| 30 mg/liter | 12.21 | 13.03 |

The results reported in Tables 8, 9 and 10 demonstrate that the salts of the S-Benzylthiouracil compounds of the present invention are as active in enhancing plant root growth as the parent molecules are.

Example 4

Mungbean Assay

The growth of the primary root of mungbean was examined in the pouch assay system. The results of the testing, presented as percent change in root length across all the free S-Benzylthiouracil compounds is shown below. The following S-Benzylthiouracil compounds have benzyl substitutions as defined in Table 11 below.

TABLE 11

The Effect of S-Benzylthiouracil Compounds with Benzyl
Ring Substitutions on Mungbean (concentrations were 10 ppm (10 mg/L))

| Compound Number | Benzyl Substitution(s) | Percent Change in Primary Root Length of Mungbean |
|---|---|---|
| Compound 2 | None | 18.9 |
| Compound 4 | 2-F | 17.7 |
| Compound 5 | 3,4-DiF | 17.6 |
| Compound 7 | 3-MeO | 17.5 |
| Compound 1 | 3-F | 10.4 |
| Compound 3 | 4-F | 10.4 |
| Compound 9 | 3-Me | 5.9 |
| Compound 6 | 3,5-DiF | 3.0 |

In Table 11, the root growth promotion in mungbean was greatest with no benzyl substitution, or halogen substituted in the ortho position or disubstituted. All of the listed compounds provided some root enhancement, however, other tested S-Benzylthiouracil compounds with benzyl substitutions reduced root growth.

TABLE 12

The Effect of S-Benzylthiouracil Compounds with Substitutions or
Changes to the Uracil Moiety on Mungbean Root Growth
(concentrations were 10 ppm (10 mg/L))

| Compound Number | Benzyl Substitution | Uracil Substitution | Percent Change in Primary Root Length of Mungbean |
|---|---|---|---|
| Compound 15 | None | 2-S-6-Me | 36.2 |
| Compound 14 | 2-Methyl | 2-S-6-Me | 15.4 |
| Compound 18 | 3-F | 2-S-6-OH | 11.3 |
| Compound 17 | 3-F | No carbonyl | 11.1 |
| Compound 11 | 3-F | 4-S | 8.9 |
| Compound 20 | 2-Cl | 2-S-6-Me | 8.2 |
| Compound 16 | 2,6-DiCl | 2-S-6-Me | 6.6 |
| Compound 10 | None | 2-S 6-OH | 5.9 |
| Compound 13 | 3-F | 2-S-5,6-imidazole | 4.5 |
| Compound 12 | 3-F | 2-S; 5-COOEt | −20.1 |

In Table 12, it can be seen that the activity of the S-Benzylthiouracil compound was doubled by the addition of a methyl group to the 6-position on the uracil ring. In contrast, a hydroxyl group on the 6-position of the uracil decreased activity by two-thirds. The combination of methylation at the 6-position on the uracil with substitutions on the benzyl ring decreased activity. Modest enhancements of root growth were observed when the uracil was modified with an imidazole in the 5,6 position, or an ethyl ester in the 5-position. Compound 12 had a significant negative effect on root growth.

TABLE 13

The Effect of S-Benzylthiouracil Compounds with Changes to the
Linkage between the Benzyl Ring and Uracil Moieties on Mungbean
Root Growth (concentrations were 10 ppm (10 mg/L))

| Compound Number | R (Benzyl Substitution) | Link | Uracil Substitution | Percent Change in Primary Root Length |
|---|---|---|---|---|
| Compound 22 | None | $CH_2CH_2S$ | 2-S | 29.0 |
| Compound 21 | 3-F | $CH_2O$ | 2-O | 9.1 |
| Compound 24 | None | $CH_2O$ | 2-O | −1.3 |

In Table 13, the results of the structure activity analysis on mungbean were unpredictable. With the 3-F benzyl substitution, changing the thioether to an ether had little effect on root growth promoting activity. In contrast, when the benzyl was unsubstituted, changing the thioether to an ether was detrimental to its root growth promoting activity. Also using the unsubstituted benzyl, increasing the length of the linkage significantly increased activity in mungbean.

Table 14 below shows that the greatest increases in mungbean root growth were observed under continuous exposure to Compound 15.

TABLE 14

The Effect of Compound 15 on Mungbean Root and
Shoot Growth at 4 Days

| Compound ppm | Root Length (cm) | Shoot Length (cm) |
|---|---|---|
| 0 (untreated control) | 6.1 | 4.9 |
| 1 | 6.9 | 5.6 |
| 10 | 8.5 | 5.0 |

Interestingly, with Compound 15 (Table 14), both root and shoot showed significant increases in growth. This assay showed that the observed enhanced root growth does not negatively affect shoot growth.

In Table 15, the effect of Compound 1 was tested in mungbean. Although Compound 1 showed strong activity in rice, only a moderate increase in root growth was observed in mungbean.

TABLE 15

The Effect of Compound 1 on Mungbean Root and
Shoot Growth at 4 Days After Sowing in Growth Pouches

| Compound ppm | Root Length (cm) | Shoot Length (cm) |
|---|---|---|
| 0 (untreated control) | 8.8 | 4.8 |
| 1 | 9.9 | 5.5 |

TABLE 15-continued

The Effect of Compound 1 on Mungbean Root and
Shoot Growth at 4 Days After Sowing in Growth Pouches

| Compound ppm | Root Length (cm) | Shoot Length (cm) |
|---|---|---|
| 10 | 10.6 | 5.2 |
| 25 | 9.5 | 4.7 |
| 50 | 5.8 | 3.9 |

Example 5

Maize Assay

The S-Benzylthiouracil compounds also induced root growth in other plant species. In maize, the effect of the sodium salt of Compound 1 was tested in the pouch assay (see Table 16 below).

TABLE 16

The Effect of the Sodium Salt of Compound 1
on Maize Root Growth 4 Days After Sowing

| Compound ppm | Root Length (cm) | Shoot Length (cm) |
|---|---|---|
| 0 (untreated control) | 12.03 | 5.39 |
| 30 | 12.63 | 4.94 |
| 100 | 9.67 | 3.46 |

Root length was increased by treatment with 30 ppm of the sodium salt of Compound 1, while higher rates resulted in root length decreases.

Example 6

Tomato Assay

In tomato, several S-Benzylthiouracil compounds were tested to determine the effects on root growth. As in mungbean, the unsubstituted S-Benzylthiouracil was active at promoting root growth (Table 17). Interestingly, tomato appears to be more tolerant of multiple halogen substitutions on the ring than either mungbean or rice.

TABLE 17

The Percent Change in Primary Tomato Root
Length Induced by Growth with S-Benzylthiouracil
Compounds Measured After 6 Days of Continuous Exposure
at a Concentration of 10 ppm

| Compound | Percent Increase |
|---|---|
| Compound 5 | 23.4 |
| Compound 2 | 23.0 |
| Compound 18 | 15.4 |
| Compound 10 | 8.4 |
| Compound 1 | 8.3 |
| Compound 3 | 2.8 |
| Compound 13 | 0.8 |
| Compound 16 | −7.2 |
| Compound 23 | −15.7 |
| Uracil | −21.0 |
| Compound 11 | −34.8 |

The unsubstituted S-Benzylthiouracil, Compound 2, was one of the most active compounds in tomato. Compounds 1-3, 5, 6, 10, 15, and 18 all enhanced root growth. However, Compounds 11, 13, 15, and 26 resulted in root growth inhibition.

TABLE 18

The Effect of Compound 2 on Tomato Growth at 6
Days After Sowing

| Compound ppm | Root Length (cm) | Shoot Length (cm) |
|---|---|---|
| 0 (untreated control) | 3.5 | 3.3 |
| 1 | 3.8 | 3.3 |
| 10 | 3.8 | 3.0 |

In Table 18, an example of a tomato experiment is shown. After 6 days in constant exposure to Compound 2, root length was increased in a dose-dependent fashion. Shoot growth was the same at 1 ppm and was not significantly reduced at 10 ppm.

Example 7

Lettuce Assay

With seed treatment, a root growth promoter may be deployed directly onto Lettuce seed, thus making it available during and immediately following germination. Following seed treatment, lettuce seed was placed in plastic boxes and incubated for 12 days in adequate moisture. In Table 19, the effect on root growth of lettuce is shown. The S-Benzylthiouracil salt shown in Table 19 increased root length.

TABLE 19

The Effect of Seed Treatment with the
Tetramethylguanidine Salt of Compound 1 on Lettuce
Root Growth at 12 Days after Planting.

| Dose of the Tetramethylguanidine Salt of Compound 1 (g/100 pounds of seed) | Mean Root Length (cm) |
|---|---|
| 0 (untreated control) | 2.5 |
| 25 | 3.2 |
| 50 | 2.7 |

Example 8

*Arabidopsis* Assay

Of increased importance for understanding mode of action, *Arabidopsis* has become the model system of choice. In Table 20, the effect of Compound 1 in growth medium on root growth of *Arabidopsis* accession Columbia is shown.

TABLE 20

The Effect of Compound 1
on *Arabidopsis* Root Growth at 6 Days
After Sowing

| Compound ppm | Root Length (cm) |
|---|---|
| 0 (untreated control) | 3.3 |
| 0.1 | 3.7 |
| 0.25 | 4.4 |
| 0.5 | 3.7 |
| 1.0 | 3.8 |

Example 9

Radish Assay

In order to determine if a root crop was sensitive to a S-Benzylthiouracil, we tested the effect of Compound 1 on radish cv. Cherry Belle (Table 21). Continuous exposure to Compound 1 resulted in increased root and shoot growth.

TABLE 21

The Effect of Compound 1 on Radish Growth at 6 Days

| Compound ppm | Root Length (cm) | Shoot Length (cm) |
|---|---|---|
| 0 (untreated control) | 3.2 | 4.0 |
| 1 | 4.1 | 4.9 |
| 10 | 3.0 | 3.3 |

Example 10

Maize Growth Promotion by Seed Treatment

Maize seeds (cultivar; Kuromochi) were treated with Compound 1 at dose rates of 0.005 grams to 0.5 gram per 100 kilogram seeds. The seeds were sown into a soil pot (one seed/pot) and then cultivated in a growth chamber at a temperature of 27° C. and a day length of 16 hours for 18 days. On the 18th day after seeding, the fresh shoot weight of each plant was examined for 3 replicates. The average weight in the group treated with compound 1 across the concentration range tested was larger than that of the untreated control group, as shown in Table 22.

TABLE 22

The Effect of Compound 1 on Maize Growth

| | Amount of Compound 1 (grams/100-kg seeds) | Average weight of the shoots (grams/plant) | Percent |
|---|---|---|---|
| Compound 1 | 0 (untreated control) | 3.8 | 100 |
| | 0.005 | 4.0 | 104 |
| | 0.05 | 5.1 | 133 |
| | 0.5 | 4.4 | 115 |

Example 11

Maize Growth Enhancement by Seed Treatment Under Low Temperature Stress

Maize seeds (cultivar; Kuromochi) were treated with Compound 1 at dose rates of 0.005 gram to 0.5 gram per 100 kilogram seeds. The seeds were sown into a soil pot (one seed/pot) and then cultivated in a growth chamber at a temperature of 27° C. and a day length of 16 hours for 10 days. On the 10th day after seeding, the plants were subjected to a temperature of 2.5° C. for 4 days at a day length of 16 hours. Following the stress treatment, they were cultivated for an additional 4 days in a growth chamber at a temperature of 27° C. and a day length of 16 hours. On the 18th day after seeding, the fresh shoot weight of each plant was measured for 5 replicates. The average weight in the group treated with Compound 1 across the concentration range tested was larger than that of the untreated control, as is shown in Table 23.

TABLE 23

The Effect of Compound 1 on Maize Growth Under Low Temperature Stress

| | Amount of compound (grams/100-kg seeds) | Average weight of the shoots (gram/plant) | Percent |
|---|---|---|---|
| Compound 1 | 0 (untreated control) | 1.50 | 100 |
| | 0.005 | 1.78 | 119 |
| | 0.05 | 2.06 | 138 |
| | 0.5 | 1.85 | 124 |

Example 12

Rice Growth Enhancement by Seed Treatment Under Low Temperature Stress

Rice seeds (cultivar; Nipponbare) were treated with the Compound 1 at dose rates of 0.5 gram to 50 grams per 100 kilogram seeds. Treated rice seeds were sown and cultivated in 2-fold diluted Kimura B hydroponic solution (Plant Science 119:39-47 (1996) in a growth chamber at a temperature of 28° C. (day)/23° C. (night) and a day length of 12 hours for 10 days.

Following hydroponic cultivation for 10 days the plants were exposed to low temperature stress at 4° C. for 6 days at a day length of 12 hours in a growth chamber. After the low temperature stress treatment, the plants were transferred to 4-fold diluted Hoagland's hydroponic solution (California Agricultural Experiment Station 1950 Circular 347 pp. 34) and cultivated for 12 days at a temperature of 28° C. and a day length of 12 hours. On the 27th day of the sequential hydroponic cultivation, each fresh shoot weight of the plant was measured for 4 replicates.

The average weights in the group treated with compound 1 over the concentration range tested were larger than that of the untreated control, as shown in Table 24.

TABLE 24

The Effect of Compound 1 on Rice Growth under Low Temperature Stress

| | Amount of compound (grams/100-kg seeds) | Average weight of the shoots (grams/plant) | Percent |
|---|---|---|---|
| Compound 1 | 0 (untreated control) | 15.4 | 100 |
| | 0.5 | 19.7 | 128 |
| | 5 | 39.8 | 258 |
| | 50 | 34.8 | 226 |

Example 13

Rice Growth Enhancement by Hydroponic Treatment Under Drought Stress

Germinated rice seeds (cultivar; Nipponbare) were cultivated in 2-fold diluted Kimura B hydroponic solution including 1 ppm of the Compound 1 and 0.01% dimethyl sulfoxide in a growth chamber at a temperature of 28° C. (day)/23° C. (night)) and a day length of 12 hours for 14 days. As an untreated control group, the plants were cultivated in the hydroponic solution without Compound 1.

Drought stress was provided by withdrawal of the hydroponic solution from the culture tube for 2 days in a growth chamber at a temperature of 28° C. (day)/23° C. (night) and a day length of 12 hours. After the drought treatment, the treated plants were cultivated in 2-fold diluted Hoagland's hydroponic solution in a growth chamber at a temperature of 28° C. (day)/23° C. (night) and a day length of 12 hours for 14 days, and then total fresh weight of the shoots of 5 plants was examined for 3 replicates. The average weight in the group treated with Compound 1 at a concentration of 1 ppm was larger than that of the untreated control, as is shown in Table 25.

TABLE 25

The Effect of Compound 1 on Rice Growth Under Drought Stress

| | Concentration of compound (ppm) | Average weight of the shoots (gram/5 plants) | Percent |
|---|---|---|---|
| Compound 1 | 0 (untreated control) | 0.43 | 100 |
| | 1 | 0.48 | 112 |

Example 14

Wheat Yield Enhancement by Foliar Spray Treatment Under High Temperature Stress

Wheat seeds (cultivar; Apogee) were sown in soil pots (5 seeds/pot) and then cultivated in a growth chamber at a temperature of 18° C. (day)/15° C. (night) and at a day length of 12 hours for 28 days. The wheat plants on the 28th day after seeding were treated by foliar spray application with a solution containing the Compound 1 at concentrations of 1 ppm to 100 ppm. As an untreated control group, the plants were treated with blank solution without Compound 1. Three seedlings per pot were used for the test. On the 2nd day after the spray application, the plants were treated with high temperature for 7 days in a growth chamber at a temperature of 36° C. (day)/32° C. (night) and a day length of 12 hours. After the stress treatment, the plants were cultivated in a growth chamber at a temperature of 18° C. (day)/15° C. (night) and a day length of 12 hours. On the 56th day after seeding, total fresh weight of young seed heads from 3 plants in each pot were measured for 8 replicates of each treatment.

The average fresh weights in the group treated with Compound 1 across the concentration range tested from 1 ppm to 100 ppm were larger than those of the untreated controls, as is shown in Table 26.

TABLE 26

The Effect of Compound 1 on Wheat Yield Under High Temperature Stress

| | Concentration of Compound 1 (ppm) | Average weight of the shoots (grams/3 plants) | Percent |
|---|---|---|---|
| Compound 1 | 0 (untreated control) | 1.68 | 100 |
| | 1 | 1.71 | 105 |
| | 10 | 1.70 | 104 |
| | 100 | 1.87 | 115 |

This study shows that yield is increased by application of a S-Benzylthiouracil compound to wheat.

We claim:
1. A method of enhancing monocotyledonous plant growth comprising applying to a plant, plant propagation material, root zone, or root of the monocotyledonous plant for which growth enhancement is sought one or more compounds selected from the group consisting of S-Benzylthiouracil compounds of Formula I:

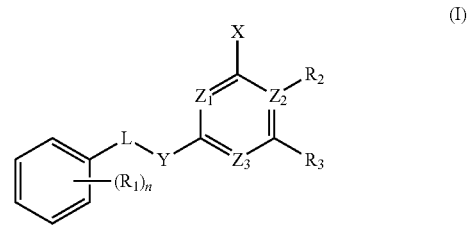

(I)

wherein X is OH, $NH_2$, or H;
Y is S or O;
$Z_1$, $Z_2$, and $Z_3$ are each carbon or N, but at least two of $Z_1$, $Z_2$, and $Z_3$ are N;
L is —$CH_2$—, —$CH_2CH_2$—, or —CH=$CHCH_2$—;
$R_3$ is H, lower alkyl, or OH; and
n is 0, 1, or 2;
wherein when n is 1, $R_1$ is H, halogen, lower alkyl, or lower alkoxy in the 2-, 3- or 4-position; and
when n is 2, each $R_1$ is independently halogen, lower alkyl or lower alkoxy;
$R_2$ is H, lower alkyl, —COO-lower alkyl, taken together with $R_3$ constitutes a —N=CH—NH— bridge forming a ring, or is absent when $Z_2$ is N; and
wherein $Z_2$ is carbon when $R_2$ is H, lower alkyl or —COO-lower alkyl and when $R_2$ and $R_3$ form a —N=CH—NH— bridge;
or a salt thereof, wherein:
when $R_1$ is methyl, X is OH, L is —$CH_2$—, and Y is S then $R_2$ and $R_3$ are not H;
when $R_1$ is Cl, $R_2$ is H, X is OH, L is —$CH_2$—, and Y is S then $R_3$ is not methyl; and
when $R_1$ and $R_2$ are H, X is OH, L is —$CH_2$—, and Y is S then $R_3$ is not OH.

2. The method of claim 1 comprising a compound of Formula I wherein n is 1 or 2, when n is 1, $R_1$ is halogen, or lower alkoxy, and when n is 2, the two substituents are halogens; L is $CH_2$, Y is S, $R_2$ is H, $R_3$ is H, $Z_1$ is N, $Z_2$ is carbon, $Z_3$ is N, and X is OH, or a salt thereof.

3. The method of claim 2 wherein the S-Benzylthiouracil compound of Formula I is selected from the group consisting of:
 a. Compound 1 wherein n is 1, $R_1$ is 3-F, L is —$CH_2$—, Y is S, $R_2$ is H, $R_3$ is H, $Z_1$ is N, $Z_2$ is carbon, $Z_3$ is N, and X is OH;
 b. Compound 2 wherein n is 0 ($R_1$ is absent), L is —$CH_2$—, Y is S, $R_2$ is H, $R_3$ is H, $Z_1$ is N, $Z_2$ is carbon, $Z_3$ is N, and X is OH;
 c. Compound 3 wherein n is 1, $R_1$ is 4-F, L is —$CH_2$—, Y is S, $R_2$ is H, $R_3$ is H, $Z_1$ is N, $Z_2$ is carbon, $Z_3$ is N, and X is OH;
 d. Compound 4 wherein n is 1, $R_1$ is 2-F, L is —$CH_2$—, Y is S, $R_2$ is H, $R_3$ is H, $Z_1$ is N, $Z_2$ is carbon, $Z_3$ is N, and X is OH, L is —$CH_2$—, Y is S, $R_2$ is H, $R_3$ is H, $Z_1$ is N, $Z_2$ is carbon, $Z_3$ is N, and X is OH;

e. Compound 5 wherein n is 2, R1 is 3,4-diF, L is —$CH_2$—, Y is S, $R_2$ is H, $R_3$ is H, $Z_1$ is N, $Z_2$ is carbon, $Z_3$ is N, and X is OH;

f. Compound 6 wherein n is 2, $R_1$ is 3,5-diF, L is —$CH_2$—, Y is S, $R_2$ is H, $R_3$ is H, $Z_1$ is N, $Z_2$ is carbon, $Z_3$ is N, and X is OH;

g. Compound 7 wherein n is 1, $R_1$ is 3-MeO, L is —$CH_2$—, Y is S, $R_2$ is H, $R_3$ is H, $Z_1$ is N, $Z_2$ is carbon, $Z_3$ is N, and X is OH; and h. Compound 8 wherein n is 1, $R_1$ is 4-MeO, L is —$CH_2$—, Y is S, $R_2$ is H, $R_3$ is H, $Z_1$ is N, $Z_2$ is carbon, $Z_3$ is N, and X is OH;

or a salt thereof.

4. The method of claim 2 wherein n is 1, $R_1$ is F, L is —$CH_2$—, Y is S, $R_2$ is H, $R_3$ is H, $Z_1$ is N, $Z_2$ is carbon, $Z_3$ is N, and X is OH, or a salt thereof.

5. The method of claim 2 wherein n is 1, $R_1$ is 3-F, L is —$CH_2$—, Y is S, $R_2$ is H, $R_3$ is H, $Z_1$ is N, $Z_2$ is carbon, $Z_3$ is N, and X is OH, or a salt thereof.

6. The method of claim 1 wherein the plant is rice, wheat, corn, barley, or sugarcane.

7. A method of enhancing dicotyledonous plant growth comprising applying to a plant, plant propagation material, root zone, or root of the dicotyledonous plant for which growth enhancement is sought one or more compounds selected from the group consisting of S-Benzylthiouracil compounds of Formula I:

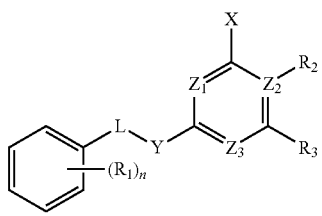

(I)

wherein X is OH, $NH_2$, or H;

Y is S or O;

$Z_1$, $Z_2$, and $Z_3$ are each carbon or N, but at least two of $Z_1$, $Z_2$, and $Z_3$ are N;

L is —$CH_2$—, —$CH_2CH_2$—, or —CH=$CHCH_2$—;

$R_3$ is H, lower alkyl, or OH; and n is 0, 1, or 2;

wherein when n is 1, $R_1$ is H, halogen, lower alkyl, or lower alkoxy in the 2-, 3- or 4-position; and when n is 2, each $R_1$ is independently halogen, lower alkyl or lower alkoxy;

$R_2$ is H, lower alkyl, —COO-lower alkyl, forms a —N=CH—NH— ring with $R_3$, or is absent when $Z_2$ is N; and wherein $Z_2$ is carbon when $R_2$ is H, lower alkyl or —COO-lower alkyl and when $R_2$ and $R_3$ form a —N=CH—NH— ring;

or a salt thereof, wherein:

when $R_1$ is F, $R_2$ and $R_3$ are H, L is —$CH_2$—, X is OH, and Y is S then $Z_2$ is not N;

when $R_1$ is F, $R_3$ is H, L is —$CH_2$—, X is OH and Y is S then $R_2$ is not ethyl formate;

when n is 2, each $R_1$ is Cl, $R_2$ is H, L is —$CH_2$— and Y is S then $R_3$ is not methyl;

when $R_1$, $R_2$ and $R_3$ are each H, X is OH, and Y is S, then L is not CH=$CHCH_2$—; and when $R_1$, $R_2$ and $R_3$ are each H, L is —$CH_2$—, and X is OH then Y is not O.

8. The method of claim 7 comprising a compound of Formula I wherein n is 1 or 2, when n is 1, $R_1$ is halogen, or lower alkoxy, and when n is 2, each $R_1$ is a halogen, L is —$CH_2$—, Y is S, $R_2$ is H, $R_3$ is H, $Z_1$ is N, $Z_2$ is carbon, $Z_3$ is N, and X is OH, or a salt thereof.

9. The method of claim 7 wherein the S-Benzylthiouracil compound of Formula I is selected from the group consisting of:

a. Compound 1 wherein n is 1, $R_1$ is 3-F, L is —$CH_2$—, Y is S, $R_2$ is H, $R_3$ is H, $Z_1$ is N, $Z_2$ is carbon, $Z_3$ is N, and X is OH;

b. Compound 2 wherein n is 0 ($R_1$ is absent), L is —$CH_2$—, Y is S, $R_2$ is H, $R_3$ is H, $Z_1$ is N, $Z_2$ is carbon, $Z_3$ is N, and X is OH;

c. Compound 3 wherein n is 1, $R_1$ is 4-F, L is —$CH_2$—, Y is S, $R_2$ is H, $R_3$ is H, $Z_1$ is N, $Z_2$ is carbon, $Z_3$ is N, and X is OH;

d. Compound 4 wherein n is 1, $R_1$ is 2-F, L is —$CH_2$—, Y is S, $R_2$ is H, $R_3$ is H, $Z_1$ is N, $Z_2$ is carbon, $Z_3$ is N, and X is OH, L is —$CH_2$—, Y is S, $R_2$ is H, $R_3$ is H, $Z_1$ is N, $Z_2$ is carbon, $Z_3$ is N, and X is OH;

e. Compound 5 wherein n is 2, $R_1$ is 3,4-diF, L is —$CH_2$—, Y is S, $R_2$ is H, $R_3$ is H, $Z_1$ is N, $Z_2$ is carbon, $Z_3$ is N, and X is OH;

f. Compound 6 wherein n is 2, $R_1$ is 3,5-diF, L is —$CH_2$—, Y is S, $R_2$ is H, $R_3$ is H, $Z_1$ is N, $Z_2$ is carbon, $Z_3$ is N, and X is OH;

g. Compound 7 wherein n is 1, $R_1$ is 3-MeO, L is —$CH_2$—, Y is S, $R_2$ is H, $R_3$ is H, $Z_1$ is N, $Z_2$ is carbon, $Z_3$ is N, and X is OH; and h. Compound 8 wherein n is 1, $R_1$ is 4-MeO, L is —$CH_2$—, Y is S, $R_2$ is H, $R_3$ is H, or a salt thereof.

10. The method of claim 7 wherein n is 1, $R_1$ is F, L is —$CH_2$—, Y is S, $R_2$ is H, $R_3$ is H, $Z_1$ is N, $Z_2$ is carbon, $Z_3$ is N, and X is OH, or a salt thereof.

11. The method of claim 7 wherein n is 1, $R_1$ is 3-F, L is —$CH_2$—, Y is S, $R_2$ is H, $R_3$ is H, $Z_1$ is N, $Z_2$ is carbon, $Z_3$ is N, and X is OH, or a salt thereof.

12. The method of claim 7 comprising the S-Benzylthiouracil compound of Formula I wherein n is 0, or n is 1 and $R_1$ is 3-F, 2-Cl, or 2-methyl, or n is 2 and $R_1$ is 2,6-diCl; L is —$CH_2$—; Y is S; $Z_1$ is N, and X is H or OH; or a salt thereof.

13. The method of claim 7 wherein the plant is mungbean, soybean, cotton, lettuce, tomato, rapeseed, radish, apple, grape, or peach.

* * * * *